United States Patent [19]

Commeyras et al.

[11] 4,221,734
[45] Sep. 9, 1980

[54] PROCESS FOR THE PREPARATION OF DERIVATIVES OF FLUOROALKANE-CARBOXYLIC AND PERFLUOROALKANE-SULFINIC ACIDS

[75] Inventors: Auguste Commeyras, Clapiers; Hubert Blancou, Montpellier; André Lantz, Oullins, all of France

[73] Assignee: Produits Chimiques Ugine Kuhlmann, Paris, France

[21] Appl. No.: 859,912

[22] Filed: Dec. 12, 1977

[30] Foreign Application Priority Data

Dec. 17, 1976 [FR] France .................... 76 38131

[51] Int. Cl.$^2$ .................... C07C 53/22; C07C 143/70; C07F 3/06
[52] U.S. Cl. .................... 260/408; 260/429.9; 260/543 R; 260/513 F; 260/513.7; 562/550; 562/605
[58] Field of Search ............. 260/539 R, 429.9, 513.7, 260/543 R, 408; 562/605, 550, 551

[56] References Cited

U.S. PATENT DOCUMENTS 4,098,806  7/1978  Commeyras et al. ................ 562/550

OTHER PUBLICATIONS

J. Chem. Soc., 1953, p. 3607, (1953).
J.A.C.S. 75, p. 4159, (1957).

*Primary Examiner*—Jane S. Myers
*Attorney, Agent, or Firm*—Pennie & Edmonds

[57] ABSTRACT

A process is disclosed for the preparation of derivatives of perfluoroalkanecarboxylic acids and perfluoroalkanesulphinic acids by reacting a perfluoroalkylhalide having the general formula $R_FX$, in which X represents an atom of chlorine, bromine, or iodine, and $R_F$ represents an unbranched or branched perfluorinated chain containing from 2 to 12 carbon atoms; with $CO_2$ or $SO_2$ in a solvent medium and in the presence of activated or unactivated zinc.

9 Claims, No Drawings

4,221,734

PROCESS FOR THE PREPARATION OF DERIVATIVES OF FLUOROALKANE-CARBOXYLIC AND PERFLUOROALKANE-SULFINIC ACIDS

BACKGROUND OF THE INVENTION

1. Field of the Invention

The present invention relates to a process for the preparation of derivatives of perfluoroalkane-carboxylic acids ($R_FCOOH$) and perfluoroalkane-sulphinic acids ($R_FSO_2H$), in which $R_F$ represents a perfluorinated branched or unbranched $C_nF_{2n+1}$ radical containing from 2 to 12 carbon atoms.

2. Description of the Prior Art

The prior art has disclosed various methods for preparation of derivatives similar to those presently disclosed. For example, it has been disclosed, hitherto, that these products may be prepared by electrofluorination, such as described in J. Chem. Soc. (1956), p. 173, in U.S. Pat. No. 2,732,398 and in Ind. Eng. Chem. (1951) 43 2332. Nevertheless, this technique is difficult to apply in practice and in the case of heavy acids, the method is characterized with very poor yields.

Chemical methods for obtaining these compounds have also been described, such as those comprising a reaction involving introduction of $CO_2$ (J. Fluorine Chem. 1974 3 247) and of $SO_2$ (J. Fluorine Chem. 1975 5 265) in perfluorinated magnesium compounds. This technique is very difficult to apply and in particular requires a reaction temperature of the order of $-40°$ C. to $-70°$ C.

The same derivatives can also be obtained according to the teachings of French Patent Application No. 76/06303 and its Certificate of Addition No. 76/37240 whereby perfluoroalkyl halides are reacted with $CO_2$ or $SO_2$ in a dimethyl sulphoxide medium and in the presence of a metallic pair, particularly the pair zinc-copper.

It has now been found that by practice of the present invention, there is provided a new process for the preparation of these derivative products, which consists in reacting perfluoroalkyl halides with $CO_2$ or $SO_2$ in a solvent medium and in the presence of zinc. The reactivity of these perfluoroalkyl halides with $SO_2$ and with $CO_2$ in the presence of zinc is quite unexpected, because from the literature (J. Chem. Soc. 1953 p. 3607 and J.A.C.S. 1957 75 p. 4159), it is known that perfluoroalkyl iodides react in a solvent medium with zinnc to give organozinc derivatives $R_F$ Zn I which are only very slightly reactive and in particular do not react either with $CO_2$ or with $SO_2$.

SUMMARY OF THE INVENTION

Generally stated, the present invention provides a method for preparing derivatives of perfluoroalkanecarboxylic acids and perfluoroalkanesulphinic acids by reacting perfluoroalkylhalides having the general formula $R_FX$ wherein X represents an atom of chlorine, bromine, or iodine, and wherein $R_F$ represents an unbranched or branched perfluorinated chain containing from 2 to 12 carbon atoms; with $CO_2$ or $SO_2$ in a solvent medium and in the presence of zinc.

The derivatives of perfluorocarboxylic acids can easily be converted into free perfluorocarboxylic acids ($R_FCOOH$) using techniques available to the art. The derivatives of perfluorosulphinic acids can be converted also by known methods into derivatives of perfluoroalkanesulphonic acids. By oxidation using oxygenated water it is possible to obtain salts of perfluorosulphonic acids, and by chlorination, the chlorides of perfluoroalkane-sulphonyl ($R_FSO_2Cl$) can be prepared which in turn can be converted into perfluorosulphonic acids ($R_FSO_3H$) by techniques well known to the art.

The present derivatives have significant utility and are commercially attractive in the industry. They can be used as acids ($R_FCOOH$ and $R_FSO_3H$), as wetting agents or surfactants. They may also be used as intermediate material for the production of oleophobizing, hydrophobizing, or soil release agents for treating textiles, leather, and paper; or for the production of products having surface-active properties.

The free acids, particularly perfluorosulphonic acids, can also be used as acid catalysts in processes such as alkylation, isomerisation of paraffins, and the like.

DESCRIPTION OF PREFERRED EMBODIMENTS

In the process of the present invention, the perfluoroalkyl halide and also the $CO_2$ or $SO_2$ are introduced into a dispersion of zinc powder in a reaction solvent. Zinc salts of the perfluorocarboxylic or perfluorosulphinic acids are thus obtained. These zinc perfluorocarboxylates can then be converted in known manner into perfluorocarboxylic acid, and the zinc perfluorosulphinates into either perfluorosulphinic acid or into perfluoroalkanesulphonyl chloride.

The starting substances which are used in the process of the invention are perfluoroalkyl halides, particularly perfluoroalkyl iodides having the general formula $C_nF_{2n+1}I$, wherein $C_nF_{2n+1}$ represents an unbranched or branched perfluoro radical containing from 2 to 12 carbon atoms.

The reaction may be carried out in numerous types of solvent. The solvents usually employed for the reactions with organometallic derivatives are perfectly suitable provided that they are not reactive in relation to the perfluoroalkyl halides. It is thus, for example, possible to use aromatic hydrocarbons such as benzene or toluene, acetonitrile, dimethyl formamide, dimethyl sulphoxide, or hexamethyl phosphotriamide. Dimethyl sulphoxide is particularly suitable and is preferred. The amounts of solvent which can be used are extremely variable and depend on the solubility of the perfluoroalkyl halides in the solvent used. The amounts used are generally between 100 and 500 ml. of solvent per mole of perfluoroalkyl halide.

The process of the invention can be carried out within a wide temperature range. In order to facilitate the performance of the process, the operation is generally carried out under atmospheric pressure and at a temperature between ambient temperature and the boiling temperature of the reactional mixture, preferably between 30° and 100° C.

It is possible to utilize substantial excesses of carbonic anhydride or sulphurous anhydride, but amounts close to the stoechiometrical amounts are sufficient. Desirably, an excess of from about 5 to 20% of these two reagents in relation to the fluorinated product is used.

The molecular ratio between the zinc and the perfluoroalkyl halide is advantageously from 1:1 to 2:1, and preferably from 1.2:1 to 1.5:1. The zinc is generally used in powder form. Commercial zinc powder can be used either untreated or treated. Thus, it is possible for the zinc to be previously activated by surface treatment, such as the treatments described in the prior art literature (Houben-Weyl 1973 XIII 2a—p. 570 and 815). The zinc may be, for example, activated by treatments with acid agents, such as those having the structures $CH_3COOH$, $HCl$, $H_2SO_4$, or the like, or the formation of alloys with other metals. In the latter case, the alloys most frequently used are those based on copper which are known under the name "zinc-copper pair". These surface treatments of the zinc, which make it possible to increase the reactivity of the zinc, are particularly advantageous in the case of the preparation of carboxylic acids, because in this case the utilization of an activated zinc results in a substantial improvement of the rate of conversion of the perfluoroalkyl halide. In the case of the reaction with $SO_2$, the activaton of the zinc is only of slight interest, because practically the same results are obtained with an untreated zinc as with an activated zinc.

The following examples illustrate practice of the invention, and should not be deemed as limiting the instant invention.

EXAMPLE 1

Preparation of $C_4F_9SO_2Cl$ 500 ml. of dimethyl sulphoxide (DMSO) and 98 g. of zinc powder are introduced into a stirred glass reactor. The mixture is heated to 40° C. and, while this temperature is maintained by external cooling, 346 g. of $C_4F_9I$ are introduced over a period of three hours while bubbling $SO_2$ into the reactional medium at a rate of flow of 8.5 liters per hour for three hours, which corresponds to about 1.06 mole of $SO_2$. At the end of the addition, the stirring of the mixture is maintained for three hours at 40° C., and then about 400 g. of DMSO is evaporated by vacuum. The residue is diluted with 500 ml. of water. A current of gaseous chlorine is introduced into this mixture at the rate of 20 liters per hour for 3 hours 45 minutes (3.1 moles) while the temperature is kept at from 35° C. to 45° C. A bottom phase is formed, which is decanted (273 g.) and which contains:

| Percentages by Weight | Ingredient |
|---|---|
| 86% | $C_4F_9SO_2Cl$ |
| 4% | $C_4F_9I$ |
| 5.3% | $C_4F_9H$ |

The rate of conversion of $C_4F_9I$ into $C_4F_9SO_2Cl$ is 73.7%. By distillation of this organic phase, a colorless liquid was obtained which distills between 101° C. and 103° C. at atmospheric pressure and which is composed of practically pure $C_4F_9SO_2Cl$.

EXAMPLE 2

Preparation of $C_2F_5SO_2Cl$ 123 g. of $C_2F_5I$ and 0.6 mole of $SO_2$ are introduced over a period of 2 hours into a reactor containing 150 ml. of DMSO and 48 g. of zinc, while the temperature is maintained at 30° C. At the end of the introduction of the reactants, the mixture is kept at 30° C. for 2 hours, and then the DMSO is evaporated by vacuum. The residue is treated with 200 ml. of water. By chlorination (2 hours at 15 liters per hour), a dense liquid phase was obtained which on distillation (boiling point 55° C.) furnished 68 g. of a colorless liquid containing 96% of $C_2F_5SO_2Cl$. The rate of conversion of $C_2F_5I$ into $C_2F_5SO_2Cl$ was 59.7%.

EXAMPLE 3

Preparation of $C_6F_{13}SO_2Cl$ 0.42 mole of $C_6F_{13}I$ (187.3 g.) and 0.46 mole of $SO_2$ are introduced over a period of two hours into a glass reactor containing a stirred mixture of 75 ml. of DMSO and 39 g. of zinc powder heated to 80° C. Throughout the reaction, the temperature is kept at 80° C. At the end of the introduction of the two reactants, heating at 80° C. is maintained for half an hour, and then 200 ml. of water are introduced. The mixture is cooled to 35° C. and chlorinated at that temperature for two and a half hours with a rate of flow of 8 liters per hour. By decantation, there are thus obtained 168 g. of lower phase containing:

| Percentages By Weight | Ingredient |
|---|---|
| 2.2% | $C_6F_{13}H$ |
| 7.6% | $C_6F_{13}I$ |
| 90% | $C_6F_{13}SO_2Cl$ |

The rate of conversion of $C_6F_{13}I$ was 93.2% and the yield of $C_6F_{13}SO_2Cl$ in relation to $C_6F_{13}I$ consumed was 92.3%. By distillation of this product, it is possible to obtain $C_6F_{13}SO_2Cl$ with a purity higher than 99.5%. The boiling point of this product was found to be equal to 58° C. at a pressure of 20 mm. mercury.

EXAMPLES 4 to 8

Preparation of $C_6F_{13}SO_2Cl$

By the same method of operation as that used for Example 3 and with the same amounts of reactants, a series of tests were carried out at 40° C. with different solvents (75 ml.). The following results were obtained.

| Example No. | Solvent | Rate of Conversion of $C_6F_{13}I$ | Yield of $C_6F_{13}SO_2Cl$ in relation to $C_6F_{13}I$ Consumed |
|---|---|---|---|
| 4 | DMSO | 95% | 87% |
| 5 | DMF | 95% | 77% |
| 6 | $CH_3CN$ | 38% | 73% |
| 7 | HMPT | 76% | 68% |
| 8 | Toluene | 9% | 15% |

EXAMPLE 9

Preparation of $C_8F_{17}SO_2Cl$ 546 g. of $C_8F_{17}I$ (1 mole) and 1.05 mole of $SO_2$ are introduced with agitation over a period of 4 hours into a glass reactor containing 97.5 g. of zinc powder (1.5 mole) and 200 ml. of DMSO, while the temperature was maintained between 50° and 55° C. Two hours after the end of the introduction, 400 ml. of water are added at 50° C. The mixture is cooled to ambient temperature, and the aqueous phase is eliminated by filtration. The solid product is taken up with 300 ml. of water and chlorinated for 4 hours at 50° C. with a rate of flow of chlorine of 24 liters per hour. By decantation in the hot state, 507 g. of liquid are obtained. This recovered liquid crystallizes in the cold state and contains:

| Percentage By Weight | Ingredient |
|---|---|
| 18% | $C_8F_{17}I$ |
| 70% | $C_8F_{17}SO_2Cl$ |

The rate of conversion of $C_8F_{17}I$ into $C_8F_{17}SO_2Cl$ was 68.5% and the yield was 82%.

EXAMPLE 10

Preparation of $C_{12}F_{25}SO_2Cl$

In the same apparatus and by the same method as that used in Example 1, the following ingredients were reacted for two hours:

| Amount | Ingredient |
|---|---|
| 0.2 mole | $C_{12}F_{25}I$ |
| 0.22 mole | $SO_2$ |
| 19 g. | zinc |
| 100 ml. | DMSO |

After the addition of the two reactants, the mixture was diluted with 300 ml. of water, cooled to 40° C., and chlorinated. 132 g. of a solid were received containing:

| Percentage By Weight | Ingredient |
|---|---|
| 26% | mixture of $C_{12}F_{25}H$ and $C_{12}F_{24}$ |
| 40% | $C_{12}F_{25}I$ |
| 20% | $C_{12}F_{25}SO_2Cl$ |

The rate of conversion of $C_{12}F_{25}I$ into $C_{12}F_{25}SO_2Cl$ was 18%.

EXAMPLE 11

Preparation of $C_6F_{13}COOH$ 187 g. of $C_6F_{13}I$ (0.42 mole) and 0.46 mole of $CO_2$ were introduced over a period of two hours into a reactor containing 40 g. of zinc powder and 75 ml. of DMSO, while the temperature was kept for 4 hours at 30° C. The reactional mixture is then taken up with 200 ml. of water and acidified with 100 ml. of concentrated hydrochloric acid. By decantation 169 g. of a liquid containing 85% of $C_6F_{13}I$ and 6% of $C_6F_{13}COOH$ are thus obtained. The rate of conversion of $C_6F_{13}I$ into $C_6F_{13}COOH$ was 6.6%.

EXAMPLE 12

Preparation of $C_6F_{13}COOH$ with the aid of a zinc-copper pair (a) Preparation of the Zn/Cu pair 2.4 g. of copper acetate $(CH_3COO)_2Cu \cdot H_2O$ are dissolved in a mixture of 200 ml. of dimethyl sulphoxide (DMSO) and 40 ml. of acetic acid kept at a temperature of from 45° C. to 50° C. After dissolving, 78 g. of zinc powder are introduced with agitation and in an atmosphere of nitrogen. The mixture is agitated for 30 minutes, and the Zn/Cu pair is then filtered and washed with 4 times 60 ml. of DMSO.

(b) Reaction of $C_6F_{13}I$ with $CO_2$ in the presence of a zinc-copper pair $CO_2$ is bubbled with a rate of flow of 6.5 liters per hour into a reactor containing 40 g. of the Zn/Cu pair dispersed in 600 ml. of DMSO. 0.4 mole of $C_6F_{13}I$ is then introduced over a period of three and a half hours while the temperature is maintained at 20° C. by external cooling. Stirring of the reactional mixture is maintained for three additional hours. The reactional mixture is then filtered, the filtrate is freed of DMSO by evaporation in vacuum, and the residue is treated with 500 ml. of 50% hydrochloric acid. By decantation, an organic phase is obtained which is distilled. 91.7 g. of perfluoroheptanoic acid are thus obtained. This acid is identified by NMR and IR spectroscopy, and also by chemical analysis ($BP_{50\,mm}$ 105° C.). The rate of conversion of $C_6F_{13}I$ into $C_6F_{13}COOH$ is 63%.

EXAMPLE 13

Preparation of $C_6F_{13}COOH$ with the aid of zinc powder activated with acetic acid The zinc powder is activated by the method described in Example 12 for the preparation of the Zn-Cu pair, except that no copper acetate is introduced. 39 g. of this zinc are subjected to the same method of operation as that employed in Example 11. 138 g. of a liquid product containing 41% of $C_6F_{13}I$ and 35% of $C_6F_{13}CO_2H$ were obtained. The rate of conversion of $C_6F_{13}I$ into $C_6F_{13}COOH$ was 31.5%.

Inasmuch as many changes and variations in detail are possible within the scope of the present invention, it is intended that the above description is presented for purposes of illustration and not by reason of limitation.

What is claimed is:

1. A process for the preparation of zinc salts of perfluoroalkanecarboxylic acid and perfluoroalkanesulphinic acid which comprises reacting a perfluoroalkyl halide having the general formula $R_FX$, wherein X represents an atom of chlorine, bromine, or iodine, and wherein $R_F$ represents an unbranched or branched perfluorinated chain containing from 2 to 12 carbon atoms; with $CO_2$ or $SO_2$ in an inert solvent medium and in the presence of a material consisting essentially of unactivated zinc the mole ratio of zinc to perfluoroalkyl halide being from 1:1 to 2:1.

2. The process according to claim 1, in which the perfluoroalkyl halide is a perfluoroalkyl iodide.

3. The process according to claim 1 in which the reactant is gaseous carbon dioxide.

4. The process according to claim 1 in which the reactant is sulphurous anhydride.

5. The process of claim 1 wherein the reaction temperature is between 30° and 100° C., and the amount of inert solvent is between 100 and 500 ml. of solvent per mole of perfluoroalkyl halide.

6. The process of claim 1 wherein the mole ratio of zinc to perfluoroalkyl halide is 1.2:1 to 1.5:1, and wherein the zinc is in powder form.

7. The process of claim 3 wherein zinc perfluorocarboxylate is recovered and reacted with acetic acid whereby perfluorocarboxylic acid is produced and recovered as the product.

8. The process of claim 4 wherein zinc perfluorosulphinate is recovered and reacted with hydrochloric acid whereby perfluoroalkylsulphonyl chloride is recovered as the product.

9. The process of claim 1 wherein the amount of $CO_2$ or $SO_2$ is from about 5 to 20% excess relative the perfluoroalkyl halide.

* * * * *